United States Patent [19]
Hwang et al.

[11] Patent Number: 5,196,452
[45] Date of Patent: Mar. 23, 1993

[54] MACROCYCLIC ANTI-VIRAL COMPOUND AND METHOD

[75] Inventors: Kou M. Hwang, Danville; You M. Qi, Redwood City; Su-Ying Liu, Belmont, all of Calif.

[73] Assignee: Genelabs Incorporated, Redwood City, Calif.

[21] Appl. No.: 647,720

[22] Filed: Jan. 29, 1991

[51] Int. Cl.$^5$ .......................................... A61K 31/185
[52] U.S. Cl. ..................................... 514/577; 514/602
[58] Field of Search ................................ 514/577, 602

[56] References Cited

FOREIGN PATENT DOCUMENTS 721103 11/1978 U.S.S.R. .

OTHER PUBLICATIONS

Grollman, A. P. and Horwitz, S. B., in "Drug Design" (E. J. Ariens, Ed.) vol. II, Chapter 7, pp. 261–272, Academic Press (1971).

Poh, B-L and Lim, C. S., Tetrahedron 46, No. 10 (1990) 3651–3658.

Poh, B-L et al., Tetrahedron 46, No. 12 (1990) 4379–4386.

Poh, B-L et al., Tetrahedron 30, No. 8 (1989) 1005–1008.

CA 75:72945h Akerfeldt et al. 1971.

*Primary Examiner*—Frederick E. Waddell
*Assistant Examiner*—Russell Travers
*Attorney, Agent, or Firm*—Peter J. Dehlinger; Carol A. Stratford

[57] ABSTRACT

A compound and method for inhibiting cell infection by an enveloped virus. The compound is a macrocyclic chromotropic acid derivative which can be substituted at a variety of naphthalene ring and bridge positions. The compound may be administered parenterally, orally, or topically for treating infection by enveloped viruses.

4 Claims, 6 Drawing Sheets

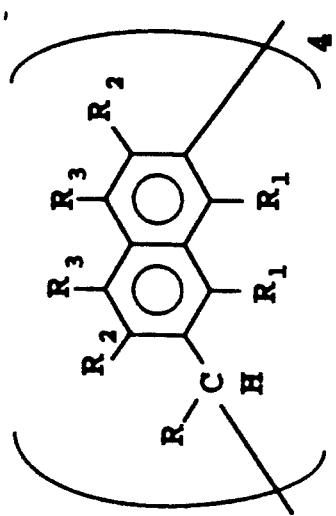
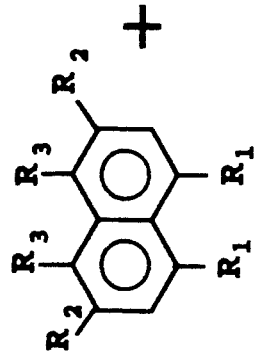
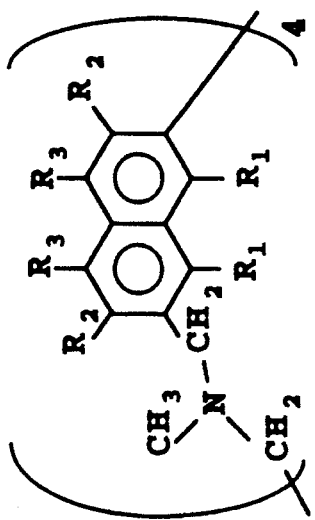
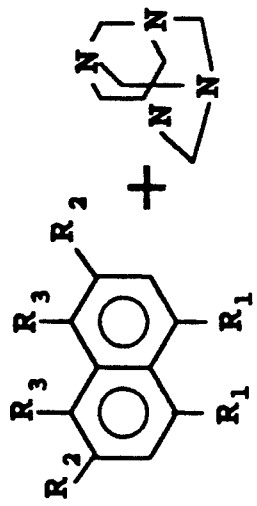
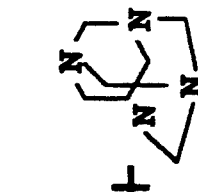
Fig. 2A
Fig. 2B

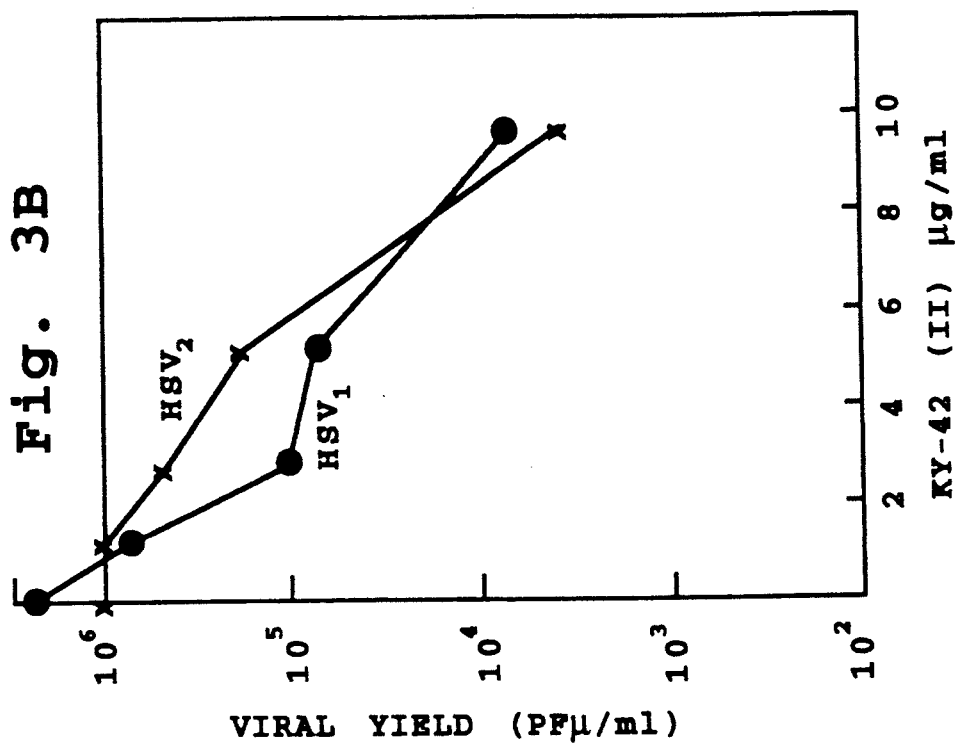
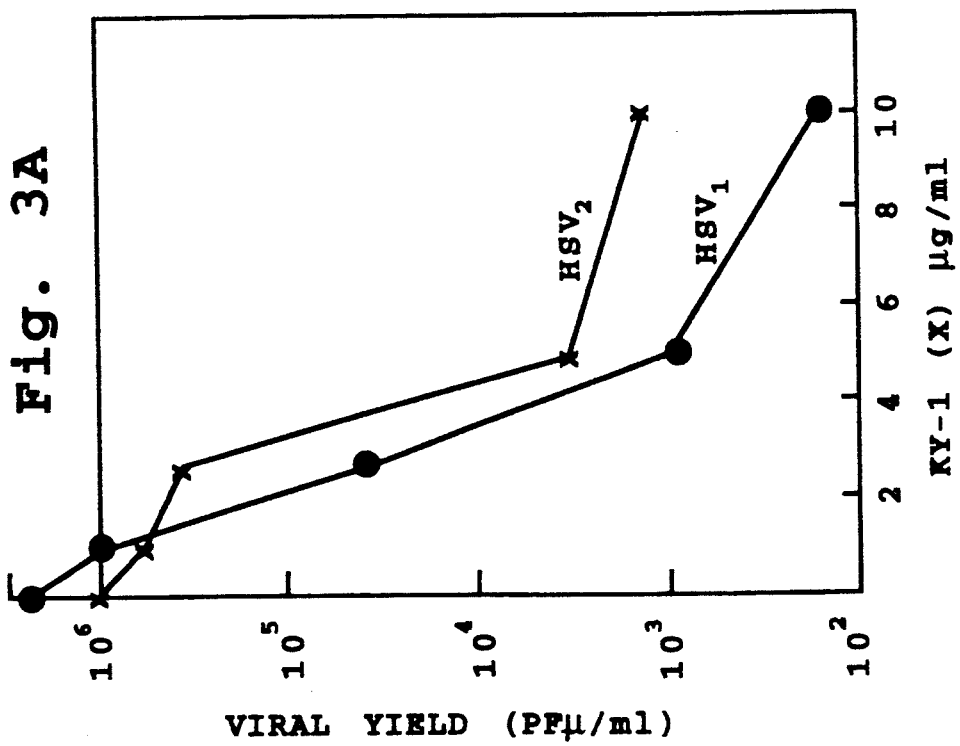

MACROCYCLIC ANTI-VIRAL COMPOUND AND METHOD

FIELD OF THE INVENTION

The present invention relates to a macrocyclic anti-viral compound and method, and in particular, to a compound and method for inhibiting cell infection by enveloped viruses.

REFERENCES

Barre-Simoussi, F., et al., Science 220:868-871 (1983).
Chanock, R. M., et al., Am.J.Hyg. 66:29-300 (1957).
Dick, E. C., Proc. Soc. Exp.Biol.Med. 127:1079-1081 (1968).
Erlich, K. S., et al., N.Eng.J.Med. 320:293-296 (1989).
Elion, G. B., et al., Proc.Natl.Acad.Sci USA 74:5617-5620 (1977).
Gibrack, C. D., et al., J.Inf.Dis. 146:673-682 (1982).
Gottlieb, M. S., et al., N.Eng.J.Med. 305:425-3 (1981).
Hansch, C. in Drug Design (E. J. Ariens, ed.), Vol. II, p. 271, Academic Press, (1971).
Hansch, C., Leo, A., Structure-Activity Correlation, Wiley, (1979).
Hilleman, M. R., Proc.Soc.Exp.Biol.Med. 85:183-188 (1954).
Huttunen, p., et al, Pharmacol Biochem & Behav 4:1733-38 (1986).
Jaffe, Chem. Rev., 53, 191 (1953).
Kern, E. R., Amer.J.Med. 73:100-108 (1982).
Klatzmann, D., et al., Science 225:59-63 (1984).
Lifson, J. D., et al., Science 241:712-716 (1988).
March, J., Advanced Organic Chemistry $3^{rd}$ ed., Chapter 9, Wiley (1985).
Mertz, G. J., et al., JAMA 260:201-206 (1988).
Mitsuya M., et al., Proc.Natl.Acad.Sci.: 82:7096-7100, USA (1985).
Po, B-L, et al., Tetrahedron Letters, 30(8):1005 (1989).
Po, B-L, et al., Tetrahedron, 46(10):3651 (1990).
Po, B-L, et al., Tetrahedron, 46(12):4379 (1990).
Popovic, M., et al. Science 224:497-500 (1984).
Roizman, B., et al, Inter. Virol. 16:201-217 (1981).
Roizman, B., et al, J. Virol. 15:75-79 (1961).
Rowe, W. P., et al., Proc.Soc.Exp.Biol.Med. 84:570-573 (953).
Smith, R. A., et al., "Ribavirin: A broad spectrum antiviral agent : In : Stapleton, T., Editor, Studies With a Broad Spectrum Antiviral Agent. International Congress and Symposium Service (London), Royal Society of Medicine, 3-23 (1986).
Spear, P. G. [Roizman, B., Editor], The Herpes Simplex Viruses, Vol. 3, Plenum Press, New York, pp. 315-356 (1989).
Stannard, L. M., et al., J. Gen. Virol., 68:715-725 (1987).

BACKGROUND OF THE INVENTION

The challenge in developing an effective therapy and prophylaxis for viral disease is to achieve inhibition of viral processes without producing extreme side effects and preferably without inducing viral resistance. Since viral replication requires use of the cellular apparatus of the host, treating virus infection by inhibiting viral replication can be lethal to the infected host cells as well. Ideally, the virus should be destroyed or inactivated in the host prior to its invasion of host cells. This is normally accomplished, with varying degrees of success, by the host's immune system, but this mechanism requires an earlier immune response, either by a prior infection or by vaccination. Further, many viruses, such as Herpes Simplex viruses (HSV) are able to effectively elude a host's immune systems, and at least one virus, the human immunodeficiency virus (HIV) is known to cripple the host's immune system (Gottlieb).

Currently, the most widely used anti-viral agents are nucleoside analogs. This class of drugs acts by disrupting viral replication, either by inhibiting enzymes required for nucleic acid processing, or by producing defective viral genome, such as by premature termination of replication. As an example, acyclovir, a purine analog used in treating a variety of viral diseases, including herpes simplex virus-1 (HSV-1) and herpes simplex virus-2 (HSV-2) inhibits viral replication at several key points, including inhibition of viral thymidine kinase and DNA polymerase, and DNA strand elongation (Elion). Ribavirin, another purine analog, is the drug of choice in treating respiratory syncytial viruses (RSV) infection. This compound appears to act by reducing cellular GTP levels, blocking the action of several GTP-dependent viral processes (Smith). To date, the most common drug treatment of HIV infection is with zidovudine (Azidothymidine; AZT), a thymidine analog which is particularly effective against human retroviruses. AZT acts with high affinity to block viral RNA-dependent DNA polymerase (reverse transcriptase), but does also block human DNA- polymerase and causes chain termination (Mitsuya).

Other nucleic acid analogs include ganciclovir, vidarabine, idoxuridine, trifluridine and foscarnet (an inorganic phosphate analog). As indicated above, all of these drugs, by blocking viral replication, also have the capacity to disrupt and normal host replication and/or DNA transcription processes as well.

Understanding of the mechanisms of infection and replication of viruses has lead to alternate drug therapies, including attempts to block viral entry into cells, alter protein synthesis at the host ribosomes, complexation of viral DNA/RNA, and immunomodulation. Interferons are glycoproteins which have complex actions including enhancement of certain immune responses as well as direct antiviral action. They are more competent in preventing infection, rather than treating established viral infection, and their use leads to undesirable problems including acute, serious discomfort, bone marrow suppression, viral resistance, and development of host immune response to the interferon.

Treatment with "anti-sense" polymers of nucleic acids is a method in which the particular viral genome is the select target. The treatment provides a highly discriminating approach which would be expected to have minimal side-effects; its use as a therapeutic is hampered by problems of targeting, introduction into cells, and the quantity of material that would be required to block each strand produced. Agents which bind to and interfere with host ribosomal protein synthesis will block viral replication. These include the toxin ricin, various plant proteins such as pokeweed anti-viral protein, alpha sarcin, and other low molecular weight compounds. The weakness with the use of these materials is their lack of selectivity. In the treatment of HIV, additional therapy has been developed by specifically targeting the unique retroviral enzyme, reverse transcriptase. Non-retroviral systems do not produce or use this enzyme, but the virus cannot replicate without it.

In some instances, understanding of structural aspects of the mechanisms of replication of viruses has provided additional drug therapies. Certain viruses, including orthomyxoviruses and paramyxovirus, herpes viruses, togaviruses and retroviruses, contain a viral envelope which surrounds the viral capsid and nucleic acid. During cell infection by an enveloped virus, the plasma membrane of the host cell is altered to include some viral-coded proteins and, as the viral nucleoprotein core exits the host cell in which it was assembled, it becomes enveloped with the modified membrane, thus forming the viral envelop. Because this structure is unique to host cells when they are virally infectious and distinct from normal cells, it can serve as an additional target for therapeutic assault.

SUMMARY OF THE INVENTION

It is one general object of the invention to provide a compound effective in inhibiting cell infection by enveloped viruses.

It is another object of the invention to provide a method of inhibiting cell infection by enveloped viruses.

The invention includes a macrocyclic antiviral compound composed of subunits of a chromotropic acid derivative linked between the 2 and 7 ring positions of adjacent subunits by methylene-linked bridges. In a general embodiment, the compound has the form:

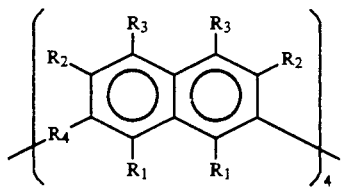

where $R_1$ is a polar, hydrogen accepting substituent, preferably OH or an uncharged, carbon-containing substituent containing a oxygen atom linked directly to the naphthalene ring, $R_2$ is sulfonic acid, a sulfonate salt, or a sulfonamide, $R_3$ is H or an uncharged or negatively charged substituent with a log (octanol/water partition coefficient) value less than 1, and $R_4$ is a 1 to 3 atom-chain bridge linking each naphthalene group through a naphthalene-ring carbon-methylene linkage, excluding the compound in which $R_1$ is OH, $R_2$ is sulfonic acid or a sulfonate salt, $R_3$ is H and $R_4$ is $>CH_2$.

In one preferred embodiment, for use particularly for use particularly in inhibiting human immunodeficiency virus (HIV) infection, $R_1$, $R_2$, $R_3$, and $R_4$ are so selected that the quantity $1.157\sigma_pR_1 + 0.113\pi R_2 - 2.060\sigma_m R_2 - 0.073\pi R_4 - 0.771$, is greater than about $-2.74$ and preferably between about $-2.7$ and $-0.9$, where $\sigma_p R_1$ is the Hammett (para) parameter (Hansch, 1979) for the substituent at the $R_1$ position, $\sigma_m R_2$ is the Hammett (meta) parameter for the substituent at the $R_2$ position, and $\pi R_2$ and $\pi R_4$ are the $\pi$ values (log(octanol/water partition coefficient values) of the substituents at the $R_2$ and $R_4$ positions, respectively.

Also included in the invention is a method of inhibiting cell infection by enveloped viruses by administering to the site of infection a therapeutically effective dose of a macrocyclic antiviral compound composed of subunits of a chromotropic acid derivative bridged between ring positions 2 and 7 (FIG. 1B) of adjacent subunits by methylene-linked bridges. Preferred macrocyclic compounds for use in the method are similar to those given above.

These and other objects and features of the invention will become more fully apparent when the following detailed description of the invention is read in conjunction with the accompanying drawings.

BRIEF DESCRIPTION OF THE DRAWINGS

FIGS. 2A and 2B illustrate two general methods of synthesis of a tetrameric macrocyclic compound;

FIGS. 3A and 3B are plots of HSV viral yields, as a function of drug dose, for the compounds KY-1 (3A) and KY-42 (3B);

DETAILED DESCRIPTION OF THE INVENTION

I. Macrocyclic Anti-Viral Compound

Figure 1:
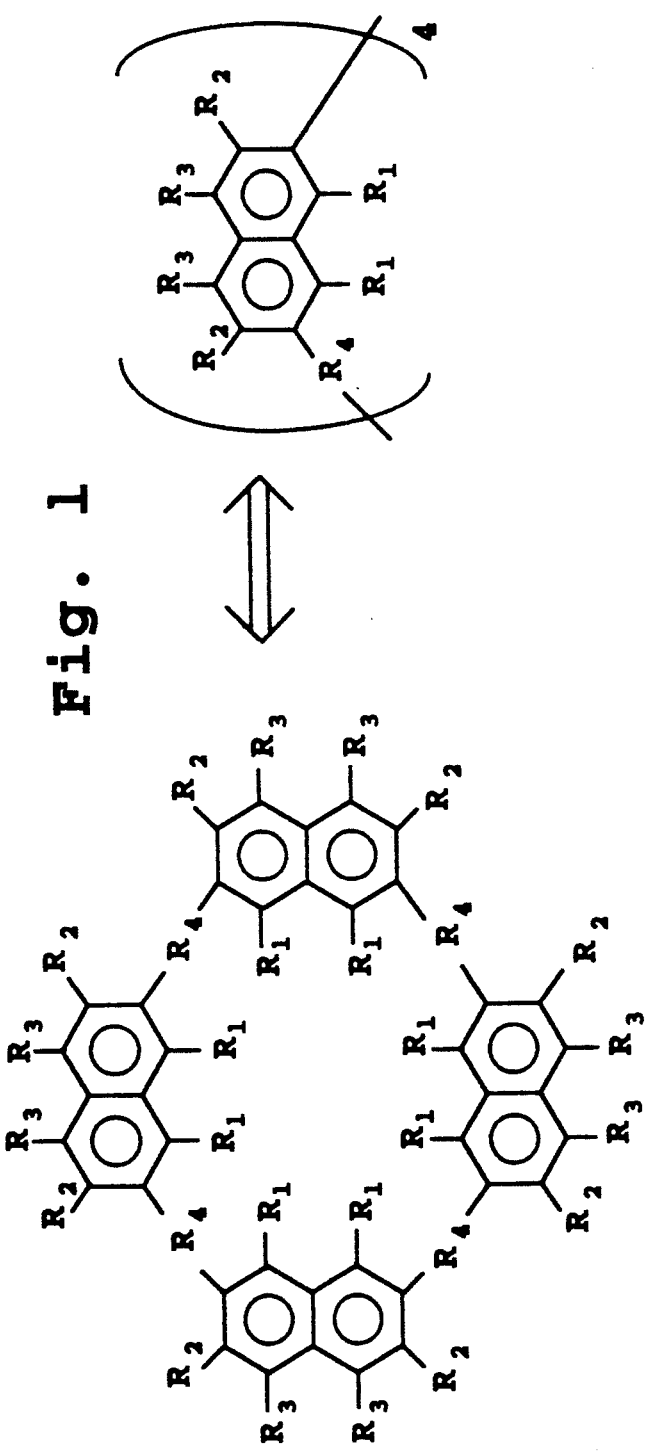
FIG. 1 shows the general structure of a tetrameric macrocyclic antiviral compound.

The invention includes, in one aspect, a macrocyclic antiviral compound composed of subunits of a chromotropic acid derivative, each subunit linked between its 2 ring position and the 7 ring position of an adjacent subunit by a methylene-linked bridge. FIG. 1 shows the general structural formula of a tetrameric macrocyclic compound formed in accordance with the invention. The subunits of a chromotropic acid derivative in the compound are represented by the structures:

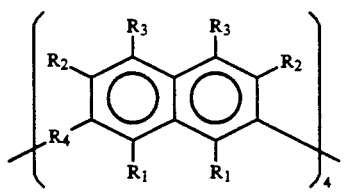

where $R_4$ represents the methylene linked bridge. As will be seen below, the invention preferably includes the chromotropic acid derivatives in which $R_1$ is a polar, hydrogen accepting substituent, preferably OH or an uncharged, carbon-containing substituent containing a oxygen atom linked directly to the naphthalene ring; $R_2$ is sulfonic acid, a sulfonate salt, or a sulfonamide; and $R_3$ is H or an uncharged or negatively charged substituent with a $\pi$, the log (octanol/water partition coefficient) value less than 1. The latter constraint is suggested by the fact that (a) in all of the compounds tested, the $\pi$ value of the substituent is less than 1, and (b) compound activity is relatively independent of chemical-group substitution at the $R_3$ position, as discussed below.

Also as will be seen below, the $R_4$ bridge linking the

The KY-1 compound is included in the method of the invention.

Representative macrocyclic compounds which have been synthesized and tested for anti-viral activity are identified by their $R_1$, $R_2$, $R_3$, and $R_4$ substituents in Table 1 below. The KY number in the lefthand column in the table refers to the analog designation of the corresponding compound. For example, the compound in which $R_1$ is OH, $R_2$ is $SO_2NH_2$, $R_3$ is H, and $R_4$ is —$CH_2$— is designated KY-3.

TABLE 1

| KY | $R_1$ | $R_2$ | $R_3$ | $R_4$ |
|---|---|---|---|---|
| 1 | OH | $SO_3Na$ | H | —$CH_2$— |
| 3 | OH | $SO_2NH_2$ | H | —$CH_2$— |
| 42 | OH | $SO_3Na$ | H | >$CHCO_2H$ |
| 48 | OH | $SO_3Na$ | H | >$CHCHOHCH_2OH$ |
| 85 | OH | $SO_3Na$ | OH | >$CHC_6H_6$ |
| 97 | OH | $SO_3Na$ | H | >$CH_2CH=CH_2$ |
| 110 | OH | $SO_3Na$ | H | >$CHC(O)CH_3$ |
| 121 | OH | $SO_2C_6H_3(OH)_2$ | H | —$CH_2$— |
| 123 | OH | $SO_2Na$ | H | —$CH_2$— |
| 143 | OH | $SO_3Na$ | OH | —$CH_2$— |
| 147 | OH | $SO_2NHCH_3$ | H | —$CH_2$— |
| 148 | OH | $SO_2NHEt$ | H | —$CH_2$— |
| 151 | $OCH_3$ | $SO_3Na$ | H | —$CH_2$— |
| 158 | OH | $SO_2CH_3$ | H | —$CH_2$— |
| 175 | OH | $SO_3CH_3$ | H | —$CH_2$— |
| 176 | OH | $SO_2NHC_6H_6$ | H | —$CH_2$— |
| 193 | OH | $SO_3Na$ | Br | >$CHBrCH_2Br$ |
| 194 | OH | $SO_3Na$ | Br | —$CH_2$— |
| 270 | $OCOCH_3$ | $SO_3Na$ | H | —$CH_2$— |
| 272 | $OCOCH_3$ | $SO_3Na$ | H | >$CHCO_2H$ |
| 276 | OCOEt | $SO_3Na$ | H | —$CH_2$— |
| 277 | OCOEtCl | $SO_3Na$ | H | —$CH_2$— |
| 280 | $OCH_3$ | $SO_3Na$ | H | —$CH_2$— |
| 281 | $OCOC_3H_7$ | $SO_3Na$ | H | —$CH_2$— |
| 284 | $OCH_3$ | $SO_3Na$ | H | >$CHCO_2H$ |
| 289 | $OCOC_4H_9$ | $SO_3NH_4$ | H | —$CH_2$— |
| 291 | $OCOC_5H_{11}$ | $SO_3NH_4$ | H | —$CH_2$— |
| 293 | $OCOCH=CHCH_3$ | $SO_3NH_4$ | H | —$CH_2$— |
| 294 | $OCO(CH_2)_6CO_2H$ | $SO_3NH_4$ | H | —$CH_2$— |
| 307 | $OCO(CH_2)_5CO_2H$ | $SO_3NH_4$ | H | —$CH_2$— |
| 313 | OH | $SO_3Ca^{\frac{1}{2}}$ | H | —$CH_2$— |
| 314 | OH | $SO_3Ba^{\frac{1}{2}}$ | H | —$CH_2$— |
| 346 | OH | $SO_3Na$ | H | —$CH_2N(CH_3)CH_2$— |
| 376 | OH | $SO_3NHCH_2CO_2H$ | H | —$CH_2$— |
| 395 | $OCH_3$ | $SO_3Na$ | H | —$CH_2N(CH_3)CH_2$— |
| 397 | $OCH_3$ | $SO_2NH2$ | H | —$CH_2$— |
| 398 | $OCH_3$ | $SO_2NHCH_2CO_2H$ | H | —$CH_2$— |
| 399 | $OCH_3$ | $SO_3NHCH_2CO_2H$ | H | —$CH_2N(CH_3)CH_2$— | chromotropic acid derivative subunits is preferably of the form >CHR, where R is H or a small carbon-containing group, such as lower alkyl, alkenyl, ketone, or carboxylic acid group, or aryl group, or of the form —$CH_2NR'CH_2$—, where R' is similarly H or a small carbon containing group, such as a lower alkyl group. In the embodiment in which $R_4$ has the form >CHR, bridged naphthalene groups are linked by a single methylene (>CH—) group. In the embodiment in which $R_4$ has the form—$CH_2NR'CH_2$—, bridged naphthalene groups are linked by the two methylene groups at opposite ends of the bridge. More generally, the chromotropic acid subunits are linked by a single methylene group forming the bridge, or by methylene groups at opposite ends of the bridge.

The compound of the invention does not include the tetrameric macrocyclic compound of chromotropic acid (4,5-dihydroxynaphthalene-2,7,disulfonic acid) linked by methylene bridges, as previously described (Po, 1989, 1990a, 1990b). This compound corresponds to KY-1 in Table 1, where which $R_1$ is OH, $R_2$ is sulfonic acid or a sulfonate salt, $R_3$ is H and $R_4$ is >$CH_2$.

FIGS. 2A and 2B illustrate two preferred synthetic methods for preparing macrocyclic chromotropic acid compounds. The method illustrated in FIG. 2A involves cyclization of a chromotropic acid derivative (which is defined herein to include chromotropic acid itself) with an aldehyde (R—CHO) to form a macrocyclic compound, such as the tetramer shown FIG. 1, in which the chromotropic acid subunits are linked by R-substituted methylene groups, i.e., in which $R_4$ is >CHR. This synthetic scheme provides a convenient method for constructing macrocyclic compounds having a variety of different bridge-methylene R groups, by carrying out the cyclization reaction in the presence of an aldehyde of the form R—CHO.

For example, to construct a macrocyclic compound with a —$CH_2$— bridge, such as the KY-1 compound, the chromotropic acid derivative is reacted with formaldehyde. Typical reaction conditions are given in Example 1A for the synthesis of KY-1. Similarly, KY-42 is prepared by cyclization with glyoxylic acid (Example 1C); KY-48, in the presence of glyceraldehyde; KY-85, in the presence of benzaldehyde; KY-97, in the presence of acrolein; and KY-110, in the presence of pyruvic aldehyde. It will be appreciated that a variety of other RCHO aldehydes having small alkyl, alkenyl, acid and other hydrocarbon R groups would be suitable. Further the R bridge group may be further modified after the cyclization reaction. For example, KY-193 may be prepared by bromination of the KY-97 compound.

In the method illustrated in FIG. 2B, cyclization of the chromotropic acid derivatives is carried out by reaction with hexamethylenetetramine, to form a 3-atom chain bridge of the type $-CH_2N(CH_3)CH_2-$. The cyclization reaction for the synthesis of KY-346 is given in Example 1K. The $-CH_2N(CH_3)CH_2-$ bridge may be modified, after the cyclization reaction, to form a variety of N-substituted bridges of the $-CH_2N(R')CH_2-$, where R' is one of a variety of small carbon-containing groups, according to known synthetic methods.

For synthesis of macrocyclic compounds with selected $R_1$, $R_2$, and $R_3$ substituents, two general approaches are available. In one approach, the chromotropic acid derivative is modified prior to cyclization so that the cyclized product will either contain the selected $R_1$, $R_2$, and $R_3$ substituent, or contain a substituent which can be readily modified to the selected substituent. This approach is illustrated by the synthesis of KY-147, which has an $SO_2NHCH_3$ $R_2$ substituent. Here the sodium salt of chromotropic acid ($R_2=SO_3Na$) was reacted first with sulfonylchloride, to form the corresponding $R_2=SO_2Cl$ derivative, which was then further reacted with methylamine to form the desired $R_2=SO_2NHCH_3$ derivative. Cyclization of the derivatized subunit with formaldehyde produces KY-147. Details of the reaction are given in Example 1E. A similar strategy was employed for the synthesis of KY-148 ($R_2=SO_2NHCH_2CH_3$) by final subunit reaction with ethylamine, and for the synthesis of KY-176 ($R_2=SO_2NHC_6H_6$) by final subunit reaction with benzyl amine.

By way of example, macrocyclic compounds with a variety of $R_1$ substituents may be prepared by modification of chromotropic acid prior to cyclization. In synthesizing KY-151 ($R_1=OCH_3$) chromotropic acid is reacted with dimethylsulfate under basic conditions, as detailed in Example 1F, to form the dimethylether of chromotropic acid. Cyclization of the derivatized subunit by reaction with formaldehyde leads to the desired macrocyclic product. Similarly, in preparing KY-307 ($R_1=O(CH_2)_5CO_2H$), chromotropic acid is first converted to the diether of hexanoic acid by initial reaction of chromotropic acid with 6-bromohexanoic acid under basic reaction conditions.

In a second general approach, the selected substituent is formed on the subunit naphthalene rings by derivatization of the naphthalene rings after cyclization to form a naphthalene-ring macrocyclic structure. For example, in preparing the compounds KY-270 through KY-294, in which $R_1$ has the form OCOR, the macrocyclic compound formed by cyclization of chromotropic acid is reacted with an acid chloride of the form RCOCl, under basic conditions, as detailed in Example 1K for the synthesis of KY-270.

This approach is further illustrated by the synthesis of KY-3 ($R_2=SO_2NH_2$). Here KY-1 was treated with chlorosulfonic acid, to form the corresponding $R_2=SO_2Cl$ compound, which was then converted to the $R_2=SO_2NH_2$ compound by reaction with ammonia. Details are given in Example 1B.

For the synthesis of KY-123 ($R_2=SO_2Na$), KY-1 is initially reacted with chlorosulfonic acid, and the resulting acid chloride derivative is reacted with sodium sulfite to reduce the sulfonate groups to sodium sulfonyl groups, as detailed in Example 1D. For the synthesis of KY-158 ($R_2=SO_2CH_3$), KY-1 is treated with sulfonylchloride to form the corresponding sulfonylchloride derivative, then reacted with sodium sulfite in the presence of bicarbonate to form the sodium sulfonyl $R_2$ groups. Further reaction with sulfonyl chloride produces the corresponding sulfonyl chloride, and with $NaOCH_3$ produces the desired $R_2=SO_2CH_3$ substituents. Reaction details are given in Example 1H. For the synthesis of KY-175 ($R_2=SO_3CH_3$), KY-1 is reacted with sulfonylchloride, as above, to produce the corresponding $R_2=SO_2Cl$ substituents. Further reaction with $NaOCH_3$ leads to the desired $R_2$ substituent. Reaction details are given in Example 1I.

The syntheses of KY-193 and KY-193 represent another example a synthetic scheme involving derivatization of the naphthalene subunits after cyclization. Here the selected macrocyclic compound, in the case, KY-1 or KY-97, is brominated with $Br_2$ under conditions which selectively brominate the $R_3$ ring positions of the naphthalene subunits.

It will be appreciated that the synthetic method for forming selected-substituent macrocyclic compounds may include both prior derivatization of chromotropic acid and subsequent derivatization of the subunits after cyclization. For example, in forming KY-397 ($R_1=OCH_3$, $R_2=SO_2NH_2$), chromotropic acid subunits are first reacted at the $R_1$ positions, to form the dimethyl ether derivative as described above. After cyclization with formaldehyde, the compound is further derivatized at the $R_2$ position, also as described above, to convert the $SO_3$ group to the desired $SO_2NH_2$ substituent.

The KY compounds described above can be converted readily to a variety of sulfonic acid or sulfonate salts, by reaction in acid or in the presence of a suitable salt, according to well known methods. Thus, for example, several of the KY compounds shown in Table 1 are ammonium salts formed by cation exchange of sodium cation in the presence of an ammonium salt, such as ammonium chloride. In addition, exposure of the macrocyclic compound to a variety of metal cations, such as the cations of Ca, Ba, Bi, Ge, Zn, La, Nd, Ni, Hf, or Pb, may produce both a metal salt and a metal chelate of the macrocyclic compound in which the metal is chelated at interior polar pocket in the compound.

The physical properties of several macrocyclic compounds prepared in accordance with the invention have been studied by absorption and mass spectrometry and by nuclear resonance spectroscopy (NMR), as detailed in Examples 1A, 1B, 1C, and 1K. These compounds are tetrameric macrocyclic compounds, such as indicated in FIG. 1, or predominantly tetrameric and octameric compounds. Macrocyclic compounds formed by cyclization of as few as three and as many as eight chromotropic acid derivative subunits are also contemplated.

II. Inhibition of Virus Infectivity

This section examines the ability of macrocyclic compounds of the invention to inhibit cell infection by a variety of enveloped and non-enveloped viruses. The enveloped viruses which were examined are the herpes viruses, Herpes simplex virus-1 (HSV-1) and herpes simplex virus-2 (HSV-2), which are double-stranded DNA viruses (Roizman); human immunodeficiency virus (HIV), an RNA retrovirus (Popovic; Barre- Simoussi); and influenza A and B and respiratory syncytial viruses (RSV), all RNA viruses (Chanock). The non-enveloped viruses which were examined include adenovirus, a double-stranded DNA virus (Rowe; Hilleman), and rhinovirus, a single-strand RNA virus (Dick). Typically, inhibition of virus infectivity was measured by the extent of inhibition of cytopathic effects detectable in infected cultured cells. Inhibition of HSV-1 and HSV-2 infectivity in cultured cells was also shown by inhibition of virus binding to infectable cells, and inhibition of viral yields in infected cells, as described below.

In addition, a large number of representative KY compounds (most of those shown in Table 1) were examined for toxicity in cell culture, using a panel of human cell lines, as detailed in Example 2. Briefly, the selected KY compound was added to cell cultures at a final concentration of 5, 10, 25, 50, or 100 $\mu$g/ml. Three days later the cells were washed to remove drug, and stained with a vital stain, to detect dead (stained) cells. The $IC_{50}$ drug concentration, i.e., value concentration of drug which produced 50% cell death, was 50 $\mu$g/ml for KY-143, KY-151, and KY-163, and 100 $\mu$g/ml or greater for all of the other KY compounds tested. For KY-1, which has a molecular weight of 1404 daltons, a drug concentration of 100 $\mu$g/ml is equivalent to about 66 $\mu$M.

A. Inhibition of HSV Infectivity

The KY compounds from Table 1 were tested for inhibition of cytopathic effects in cultured, HSV-infected cells. In the method reported in Example 3, Vero cells were infected with HSV-1 or HSV-2 and allowed to grow in culture until cytopathic effects were clearly visible. In the absence of infection, the cells form an even monolayer of fibroblast-like cells. With HSV infection, a cytopathic effect characterized by round cells in suspension is clearly evident after 24 hours, followed by clumping and lysis of infected cells after 24-72 hours.

In the drug inhibition study reported in Example 3, cells were exposed to HSV-1 or HSV-2 virus and, at the same time, to a selected KY drug, at a final drug concentration of 10 $\mu$g/ml. Twenty-four hours later the cells were examined for cytopathic effect. If a clear cytopathic effect was not observed with 10 $\mu$g/ml of the drug, the study was repeated at a drug concentration of 20 $\mu$g/ml. All of the compounds listed in Table 2 gave clear cytopathic effects at a drug concentration of 10 or 20 $\mu$g/ml.

The compounds in Table 2 were further tested for activity against HSV infection in a plaque reduction assay, as detailed in Example 4. Briefly, Vero cells, after overnight incubation, were exposed to serial dilutions of KY compound, from 0.625-10 $\mu$g/ml, and HSV-1 or HSV-2 virus for two hours. After washing to remove drug and extracellular virus, the cells were further incubated for days, then stained and counted for plaque formation. Percent inhibition was determined by dividing plaques produced by total number of plaques in infected, untreated controls. From the dose response curve of plaques (expressed as percent of control), the dose required to produce 50% plaque reduction, $ED_{50}$, was determined. The $ED_{50}$ values for infection by HSV-1 and HSV-2 infection are shown in Table 2. The calculated $ED_{50}$ values were used in structure/activity analysis, described below, to determine the chemical-group substituent properties which are related to anti-HSV-1 and anti-HSV-2 activity.

TABLE 2

| KY | $ED_{50}$ ($\mu$g/ml) HSV-1 | HSV-2 |
|---|---|---|
| 1 | 2.7 | 1.7 |
| 3 | 2.5 | 1.8 |
| 121 | 1.5 | 1.8 |
| 123 | 1.5 | 2.5 |
| 151 | 1.2 | 1.8 |
| 194 | 1.0 | 1.0 |
| 270 | 2.0 | 2.0 |
| 276 | 1.3 | 1.2 |
| 277 | 1.0 | 1.2 |
| 280 | 1.1 | 1.0 |
| 281 | 0.5 | 1.5 |
| 284 | 1.0 | 1.6 |
| 289 | 2.2 | 1.7 |
| 291 | 1.4 | 2.0 |
| 293 | 1.9 | 2.7 |
| 294 | 1.0 | 2.2 |
| 307 | 0.7 | 2 |
| 376 | 2.7 | 1 |

With reference to Tables 1 and 2, it is seen that compounds with highest anti-HSV activity (the compounds in Table 2, which inhibit CPE effects in Vero cells at a drug concentration of less than 10-20 $\mu$g/ml) have the following chemical-group substituents: $R_1$ is a polar substituent which is able to hydrogen bond. Exemplary substituents are OH, alkoxy groups, such as $OCH_3$ or an ester, such as $OCOCH_3$, and esters of larger organic groups. $R_2$ is a sulfonic acid, sulfonate salt, or sulfonamide. $R_3$ is H or a halide (e.g., Br), and more generally, a substituent with a log(octanol/water partition coefficient) value less than 1, as given in Table IV-I of Hansch. Compounds having a variety of $R_4$ groups of the form >CHR, where R is a lower alkyl, alkenyl, ketone, or carboxylic acid, as well $R_4$ groups of the form—$CH_2N(CH_3)CH_2$— are active in inhibiting HSV infectivity.

The ability of selected KY compounds to inhibit HSV-1 and HSV-2 viral yield at selected drug concentrations up to 10 $\mu$g/ml was assessed in the viral inhibition assay described in Example 5. Briefly, cultured Hela cells were exposed to serially diluted KY compound and virus, allowed to grow for 24 hours, then freeze/thawed 3 times to release virus particles. Vero cells were infected serial dilutions of the viral lysates were assayed for plaque counts as above. The drop in viral yield, as a function of drug concentration, is plotted in FIGS. 3A and 3B for compounds KY-1 and KY-42 respectively. The dose dependent drop in viral yield was between about 3-5 orders of magnitude, depending on drug and virus. The degree of inhibition of viral yield was generally greater for HSV-1 than for HSV-2. Similar results were observed with several other KY compounds.

The inhibitory effect of KY-1 against drug-resistant strains of HSV-1 and HSV-2 was compared with several anti-viral agents which have been used in treating HSV infection. These compounds tested were the nucleoside analogs acyclovir (ACV), ganciclovir (DHPG), phosphonoformate (PFA), and phosphomethoxyethyladenine (PMEA). Inhibition of viral yield was determined, as above, by infecting Hela cells in the presence of wild type or drug-resistant strains of HSV-1 or HSV-2, and serial dilutions of a selected anti-viral compound, and infecting Vero cells with serial dilutions of the Hela cell lysate, as above. Details of the inhibition study are given in Example 6.

The $ID_{90}$ concentration which effects 90% inhibition of viral yield is given in Table 3. The KOS (HSV-1) and 333 (HSV-2) are wild type viruses; the KOS(PMEA)' and KOS(PFA)' are drug-resistant HSV-1 strains having a DNA polymerase mutation. The 333(DHPG) strain is a drug-resistant HSV-2 strain having a thymidine kinase mutation. With the exception of DHPG as an inhibitor of drug-resistant strains of HSV-1, and PMEA as an inhibitor of drug-resistant strains of HSV-2, all of the nucleoside analogs were at least about 20 times less active against drug-resistant strains than wildtype strains of either HSV-1 or HSV-2, as measured by drug concentration required to inhibit yield. By contrast, the KY compound showed substantially the same specific activity against drug-resistant strains of HSV-1 and HSV-2 as against wildtype strains.

TABLE 3

| Virus | Strain/ drug selection | Mutation Locus | Drug tested ($ID_{90}$)# | | | | |
|---|---|---|---|---|---|---|---|
| | | | KY-1 (ug/ml) | ACV (uM) | DHPG (uM) | PFA (uM) | PMEA (uM) |
| HSV-1 | KOS | None | 1.9 | 14 | 2 | 180 | 100 |
| | KOS(PMEA)' | DNA pol | 2.6 | 380 | NT | 3000 | >2000 |
| | KOS(PFA)' | DNA pol | 4.3 | 100 | 1 | >1000 | >1000 |
| HSV-2 | 333 | None | 3.2 | ≈10 | 2 | 150 | 155 |
| | 333(DHPG)' | TK | 3.7 | >100 | 215 | NT | 120 |

The data demonstrate that KY-1 is effective against drug-resistant HSV strains at drug concentrations comparable to those which are effective against wild type virus strains. By contrast, and with the exception of DHPG as an inhibitor of HSV-1 strains, both drug-resistant strains showed a significant resistance to ACV, DHPG, PFA, and PMEA, as evidenced by the several-fold greater $ID_{90}$ drug concentrations required for virus inhibition.

A number of studies reported in co-owned U.S. patent application for "Treatment of Herpes Simplex Virus Infection", indicate that the KY compounds bind selectively to viral envelop proteins, and that this binding blocks virus attachment to infectable cells, thereby inhibiting virus infectivity.

Figure 4:
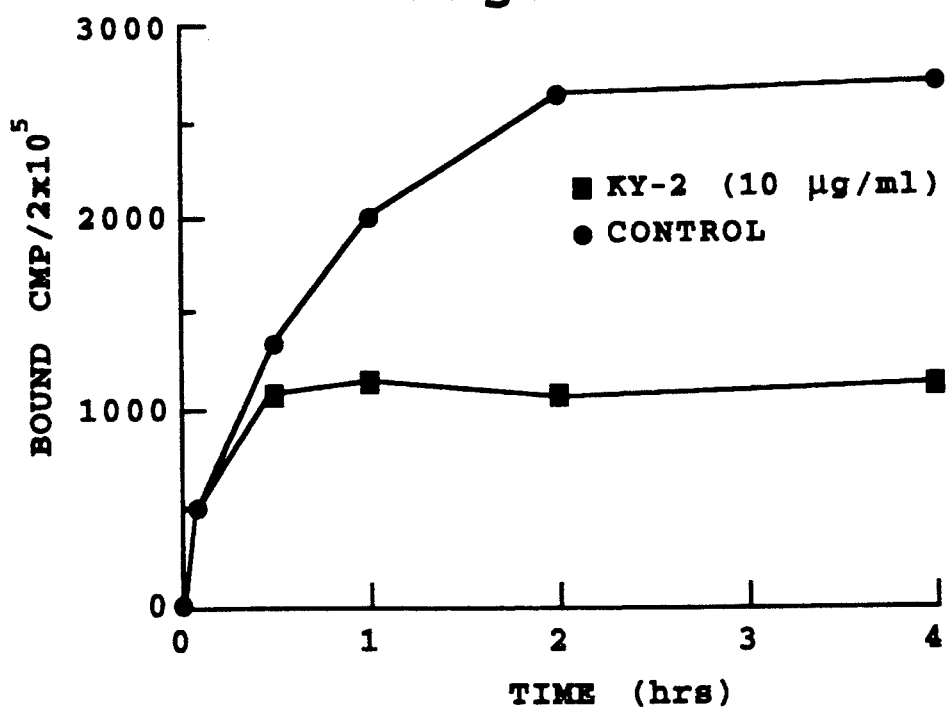
FIG. 4 shows the inhibition of $^3$H-labeled HSV-1 binding to cells by the compound KY-1.

In one study, the ability of a KY macrocyclic compound to block HSV binding to infectable cells was examined. Briefly, Vero cells were exposed to radiolabeled HSV-1 or HSV-2 in the absence of KY compound or in the presence of 10 µg/ml KY-1, and binding of the virus at times up to 4 hours after exposure to the virus was measured. FIG. 4 shows a plot of virus (radiolabel) binding to cells over the four-hour incubation period. In the absence of drug, the amount of bound virus increased steadily over two hours, and slightly from 2–4 hours. By contrast, virus binding to cells peaked at about ½ hour in the presence of drug, presumably reflecting the time during which the binding events effective to block virus binding to the cells are equilibrating.

Figure 5:
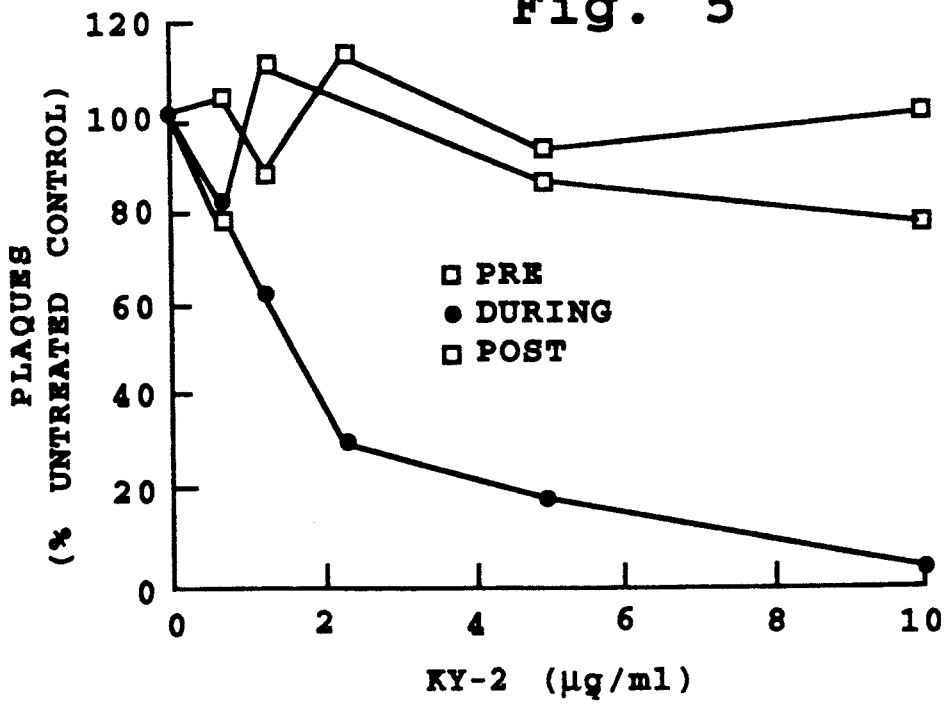
FIG. 5 is a plot of the inhibition in plaque formation of HSV-1 virus when the virus is exposed to the compound KY-1 before (open squares), (ii) after (closed squares), and during (closed circles) incubation with Vero cells.

In a second study, the effect of compound when administered prior to, during, or after cell infection by HSV-1 was examined. In these studies, cells were exposed to one of a series of increasing KY-2 concentrations, and the extent of infection was measured by number of plaques observed 24 hours after infection. The reduction in plaque formation, expressed as a percent of control, is shown in FIG. 5 for cells treated with drug prior to (solid rectangles), during (closed circles), and after (open rectangles). Significant virus inhibition was seen only when the cells were treated with drug during exposure to virus, indicating that virus inhibition occurs at the period of virus binding to and entry into infectable cells.

In a third study, purified HSV-1 virus suspensions were incubated with KY-1 or the sodium salt thereof, or a control solution for 1 hour, then serially diluted to drug concentrations between $10^1$ to $10^{-4}$ µg/ml. Addition of the serially diluted virus suspensions gave the plaque counts, measured in duplicate, shown in Table 4. The "X" symbol in the table indicates plaques too numerous to count. The results of the study demonstrate that inhibition of HSV infection by KY compounds is due, at least in part, to binding of drug to HSV particles. Further, complete virus inhibition was seen at drug final drug concentration of $10^{-2}$ to $10^{-4}$ µg/ml (which are much lower than those needed to inhibit HSV in Vero cell culture). It can be concluded that the drug-binding-/inaction of the virus is effectively irreversible, i.e., not reversed by high dilution effects.

TABLE 4

| KY Compounds | Initial Viral Input (pfu/cell) | Plaque number after serial 10-time dilutions | | | | | |
|---|---|---|---|---|---|---|---|
| | | 1 | $10^1$ | $10^2$ | $10^3$ | $10^4$ | $10^5$ |
| Control | 0.3 | XX | XX | XX | 50,41 | 9,4 | 0,0 |
| (media only) | 3 | XX | XX | XX | XX | 38,49 | 8,4 |
| KY 1 | 0.3 | 3,2 | 0,0 | 0,0 | 0,0 | 0,0 | 0,0 |
| (10 µg/ml) | 3 | 2,2 | 2,1 | 17,16 | 5,2 | 0,0 | 0,0 |
| KY 217 | 0.3 | 2,8 | 3,3 | 0,0 | 0,0 | 0,0 | 0,0 |
| (10 µg/ml) | 3 | XX | XX | 6,0 | 5,5 | 0,0 | 0,0 |

Figure 6:
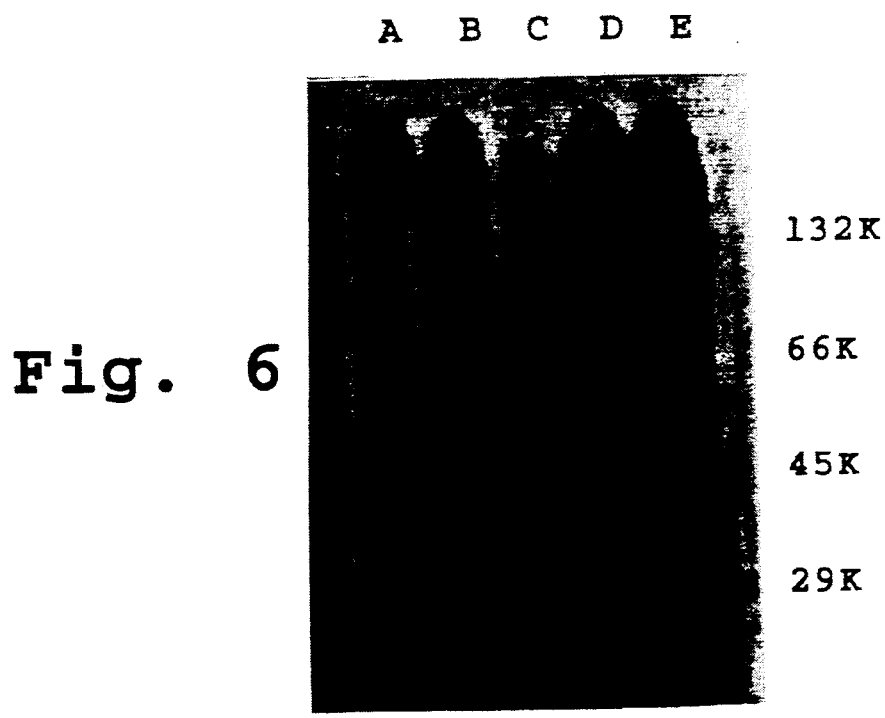
FIG. 6 shows SDS-PAGE autoradiograms of HSV-1 proteins in the presence (lane A) and absence (lane B) of mercaptoethanol, and of HSV-2 proteins in the presence (lane C) and absence (lane D) of mercaptoethanol, all with bound radiolabeled KY-1, and stained marker proteins (lane E)

In a fourth study, the binding of radiolabeled KY-1 compound to HSV-1 and HSV-2 viral proteins was examined. After compound binding, virus proteins then fractionated by sodium dodecyl sulfate polyacrylamide gel electrophoresis (SDS-PAGE), and the gel patterns developed by autoradiography. In FIG. 6, lanes A and B in the figure are autoradiographs of HSV-1 proteins in the presence (lane B) and absence (lane B) of mercaptoethanol, and lanes C and D, analogous patterns for HSV-2 proteins. The lane at the right contains the molecular weight markers, as indicated. The major bands of drug binding in HSV-1 have molecular weights, as determined from SDSPAGE, of 45, 66, and about 130 kilodaltons. The major bands of drug binding in HSV-2 have similar molecular weights. The major bands which show KY binding in FIG. 6 correspond in molecular weight, to HSV glycoproteins gD, gB, and gC.

B. Inhibition of RSV and Influenza A Virus Infectivity

Representative KY compounds from Table 1 were tested for inhibition of cytopathic effects in cultured MDCK or HEp2 cells after infection by Influenza A virus (A/Taiwan strain) or RSV virus. In the method of inhibiting virus infectivity by influenza A, MDCK cells were infected with the virus, and the cells were allowed to grow in culture until cytopathic effects were clearly visible. In the absence of infection, the cells form an even monolayer of fibroblast-like cells. With virus infection, a cytopathic effect characterized by cell clumping is observed. For each compound tested, drug concentrations of 0.1, 1, 10, 25, and 100 μg/ml were added to cultured cells at the time of virus infection, as detailed in Example 7. Twenty-four hours later the cells were examined for percent clumping, based on the percent of clumped cells of total cell particles in a given view field. The inhibition of clumping was plotted as a function of drug concentration, to determine the dose effective to produce a 50% reduction in the percent clumped cells, measured with respect to control (no drug treatment). The measured $ED_{50}$ values are given in Table 5 below.

A similar method was employed to determine the $ED_{50}$ of RSV inhibition of cytopathic effect (cell clumping) in HEp2 cells, with the results shown in Table 5. Details are given in Example 8.

TABLE 5

| Compound | $ED_{50}$ (μg/ml) Influenza A/Taiwan | RSV |
|---|---|---|
| KY-1 | >188 | 0.19 |
| KY-3 | 6 | 0.75 |
| KY-42 | 94 | 1.50 |
| KY-47 | 94 | >250 |
| KY-85 | >250 | 1 |
| KY-97 | 5 | 0.5 |
| KY-110 | >250 | 4 |
| KY-123 | 31.3 | 1 |
| KY-151 | >94 | 1.5 |
| KY-193 | 5.0 | 0.8 |
| KY-194 | 7.9 | 0.5 |

C. Inhibition of HIV Infectivity

Representative KY compounds from Table 1 were tested for inhibition of cytopathic effects in cells infected with one of two HTLV-III strains, HTLV-III$_B$ and RF-II strains, as described in Example 9. Briefly, cells chronically infected with HTLV-III$_B$ or RF-II HIV strains were incubated in the presence of serial dilutions of the selected KY compound, then further cocultured with indicator cells. The extent of syncytia formation was scored under phase microscopy. The concentration effective to produce complete inhibition of syncytia formation, $ED_{100}$, is shown in Table 6 for the two HIV strains. The blank in a column means that the compound was not tested for that compound. Data are presented as Log (1/$ED_{100}$), where $ED_{100}$ represents that concentration (μg/ml) effective to completely inhibit cell syncytia formation, as detailed in Example 9.

TABLE 6

| Compound | LOG (1/$ED_{100}$) HTLV-III$_B$ | RF-II |
|---|---|---|
| KY-1 | −.9 | |
| KY-42 | −.9 | |
| KY-48 | −2.4 | |
| KY-85 | −1.5 | |
| KY-97 | −1.5 | |
| KY-110 | −1.5 | |
| KY-123 | −1.2 | |
| KY-143 | −2.1 | |
| KY-147 | −2.4 | |
| KY-148 | −2.4 | |
| KY-151 | −.9 | −1.5 |
| KY-158 | −2.7 | −2.7 |
| KY-175 | −1.8 | −2.4 |
| KY-176 | −2.1 | −2.4 |
| KY-193 | −1.8 | |
| KY-194 | −1.8 | −2.1 |
| KY-270 | −1.2 | −1.5 |
| KY-276 | −1.2 | −1.5 |

TABLE 6-continued

| Compound | LOG (1/$ED_{100}$) HTLV-III$_B$ | RF-II |
|---|---|---|
| KY-277 | −1.2 | −1.5 |
| KY-284 | −1.2 | −1.5 |
| KY-291 | −.9 | −1.5 |
| KY-293 | −1.2 | −1.8 |
| KY-294 | −.9 | −1.2 |

As seen, there is a general correlation between antiviral activity against the two strains; that is, compounds which are most active against the HTLV-III$_B$ strain are also most active against the RF-II strain.

D. Effect on Non-Enveloped viruses The ability of KY compounds to inhibit cell infection by a rhinovirus and adenoviruses 5 and 7 which are non-enveloped viruses, was similarly studied. Vero cells ($10^5$) were infected with a rhinovirus in the presence of KY-1, at concentrations ranging between 1–100 μg. Twenty-four hours after virus infection, the cells were examined for cytopathic effect, evidencing viral infection. No reduction in cell clumping was observed at any of the KY drug concentrations.

Vero cells were infected with adenovirus in the presence of KY-1, also at concentrations ranging between 1–100 μg, and twenty-four hours after virus infection, the cells were examined for cytopathic effect. No reduction in cell clumping was observed at any of the KY-1 drug concentrations.

In summary, a broad range of KY compounds are effective inhibitors of cell infection by each of the several enveloped viruses which were studied. Binding studies carried out in particular with respect to HSV viruses indicate that the anti-viral activity of the compounds is dependent on binding to virus envelop components, which in turn inhibits virus attachment to infectable cells. The apparent inability of the compounds to inhibit infection of non-enveloped viruses is consistent with this mechanism.

III. Quantitative Structure Activity Relationships

The bioactivity of drug compounds can be quantitatively correlated with at least one, and typically two or more attributes of the drug molecule, such as the partitioning of the compound between hydrophilic and hydrophobic environments, expressed as its partition coefficient (P), the size or shape, often expressed in terms of molecular volume and surface area or steric parameters ($E_s$), the electronic nature of a system containing delocalized π electrons, and the overall effects of electronic distribution including the net atomic charge, dipole moment, and bond order or strength, and spatial relationships between key atoms in the molecule.

With respect to electronic parameters, the effect of chemical-group substitutions on π electron systems have been well studied. Substituents generally will enlarge or distort these electron clouds; if the added group contains available electrons which occupy properly oriented orbitals, the delocalization will be extended; if the added species is either electron-withdrawing or electron-donating, the π cloud will be distorted. Molecular orbital (MO) theory provides calculational methods which quantitatively interpret the effects of such substitutions.

One such parameter, the Hammett parameter σ, is a measure of the electronic influence of chemical-group substituents on the reactivity of another group on the molecule; the two groups are isolated physically but communicate electronically through a delocalized $\pi$-electron system. Hammett $\sigma$ values are determined by measuring the effect of substituents on the dissociation of benzoic acid in water at 25° C. (March), and have been successfully applied to predictions for other aromatic ring systems. The effect of a substituent varies depending on its location; if it is located meta relative to the affected site, the value is reported as $\sigma_m$, or if it is para, $\sigma_p$. When a substitution is placed in the ortho (adjacent) position, intramolecular interactions introduce complications, these cases must be individually determined (Richardson).

Analogously, methods have been developed which allow quantification and prediction of many of the physical properties of molecules. For example, the partitioning of a chemical species between immiscible solvents is expressed mathematically as the partition coefficient (P), it is a measured classically (Hansch) by the determination of its distribution between octanol and water ($P_o$), the ratio is expressed in the log form. The effect on the partition coefficient can be predicted with reasonable accuracy from the properties of the atom or fragment which is added. Usually the partition coefficient of an added substituent is normalized by the coefficient of the unsubstituted ("parent") molecule and termed "$\pi$". LogP and $\pi$ can be determined either by direct measurement or calculation from tabulated factors by the fragment method (Hansch).

It will be appreciated that the contributions to the partition coefficient and electronic parameters of a drug molecule will be cumulative with respect to the chemical-group substitutions in the compound. For example, the addition of a given chemical-group substituent to an aromatic ring system will likely alter the partition coefficient of the compound, and if it is electron-donating or withdrawing, will alter the molecular orbital energies and charges on the atoms in a conjugated electron system. Any corresponding changes in bioactivity may be occurring as a consequence of either the modification in an isolated parameter or the synergism of more than one.

The method of quantitative structure-activity relationship (QSAR) analysis (Hansch), has shown that frequently there is a correlation between a selected bioactivity of a compound and parameters characterizing the solubility and electronic properties of the substituents, and that this can be expressed in a relatively simple mathematical formula of the general type:

$$-\text{Log(Activity)} = a\text{Log}(P)^2 + b\text{Log}(P) + c\sigma + d \quad (1)$$

where P and $\sigma$ are only shown as model parameters, which may alternatively, or additionally include such parameters as steric factors or molecular orbital energies. By determining the parameter values for each of the members of a group of active compounds, the coefficients (e.g., a, b, c and d) of the QSAR equation can be found by multivariate linear regression to a least squares fit of the parameters with the trend of the measured activities. Activity is typically defined as the concentration of compound required to achieve a defined effect, for example, the concentration of a drug which produces a 50% inhibition or a 90% inhibition of a measurable biological effect.

In the following QSAR analysis, changes observed in the anti-HIV (Is1) from Table 6 were correlated with changes in structure introduced by substitutions at one to four separate positions about the molecular framework. The substitutions which produced the compounds which were analyzed are described in the accompanying table (Table 1). The physical predictors included for each of the $R_1$–$R_4$ substituents were: (1) $\pi$, defined as the log of the calculated partition coefficient of an individual substituent (Hansch 1979); (2) $\pi^2$; (3) V, the molecular volume of each substituent; and (4) A, the area of the molecular volume V. For substituents $R_2$–$R_4$, which are positioned on the aromatic naphthalene ring, the additional $\sigma_m$ and $\sigma_p$ predictors were included. The $\sigma$ values were obtained from published tables (Hansch). Area and volume parameters were calculated using a modified molecular volume program obtained from the Quantum Chemistry Program Exchange (Bloomington, Ind.), with an energy minimized molecular structure as input.

Multi-variate regression analysis was performed using a computer program which systematically tested each combination of up to four variables (the maximum number of variables supported by the 23 activity values included in the analysis). Since A and V and $\sigma_m$ and $\sigma_p$ strongly correlate with one another, combinations of predictors containing both members of either of these two pairs of predictors, e.g., A and V, were excluded. The regression equations which were generated were then sorted on the basis of (a) highest squared multiple R (a measure of degree to which the measured activity is accounted for by the equation) and (b) correlation between parameters (the degree to which parameters in the equations are independent) less than 0.8.

The following equation gives the best fit to the $ED_{50}$ activity for inhibition of HIV:

$$-\text{Log}_{10}\text{Activity} = 1.157\sigma_p R_1 + 0.113\pi R_2 - 2.060\sigma_m R_2 - 0.073\pi R_4 - 0.771.$$

(n = 23, multiple R = 0.743, squared multiple R = 0.552, residual = 3.197 and F-ratio = 5.545)

Figure 7:
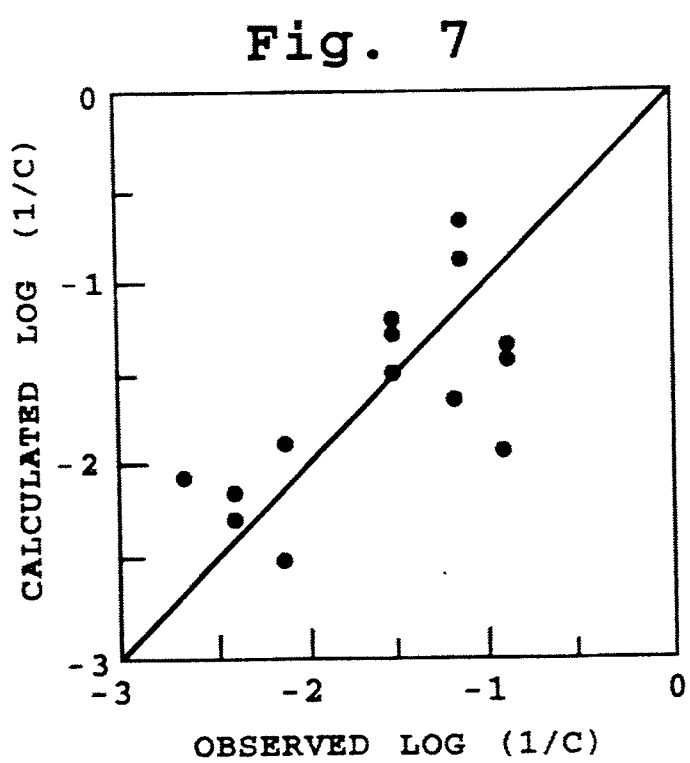
FIG. 7 is a plot comparing actual HIV inhibitory activities of KY compounds and values predicted from a linear regression equation of activities based on structure/activity relationships.

The statistical value which describes the influence of the selected parameters on the observed activity is squared multiple R. For the data in this set, about 55% of the variation in anti-HIV activity is explained; that is, the five terms in the QSAR equation account for about 55% of the activity. By using the values of the parameters of the compounds which were actually tested in the equation, it is possible to calculate an activity value based on the regression equation; a comparison of the agreement of the calculated and observed activities for the twenty-six KY compounds is given at the righthand columns in Table 7 below, and also plotted in FIG. 7. The line in the figure represents ideal agreement between measured and predicted activity (slope = 1). It can be seen that there is good consensus, with most points close to the line.

TABLE 7

| KY# | $\sigma_p R_1$ | $\pi R_2$ | $\sigma_m R_2$ | $\pi R_4$ |
|---|---|---|---|---|
| 1 | −0.37 | −4.82 | −0.10 | 0.42 |
| 42 | −0.37 | −4.82 | −0.10 | −4.77 |
| 48 | −0.37 | −4.82 | −0.10 | −0.61 |
| 85 | −0.37 | −4.82 | −0.10 | 2.20 |
| 97 | −0.37 | −4.82 | −0.10 | 1.61 |
| 110 | −0.37 | −4.82 | −0.10 | −0.83 |
| 123 | −0.37 | −1.82 | −0.10 | 0.42 |
| 143 | −0.37 | −4.82 | −0.10 | 0.42 |
| 147 | −0.37 | −1.22 | 0.46 | 0.42 |
| 148 | −0.37 | −4.82 | −0.10 | 0.42 |

TABLE 7-continued

| KY# | $\sigma_p R_1$ | $\pi R_2$ | $\sigma_m R_2$ | $\pi R_4$ |
|---|---|---|---|---|
| 151 | −0.27 | −4.82 | −0.10 | 0.42 |
| 158 | −0.27 | −1.63 | 0.60 | 0.42 |
| 175 | −0.27 | −0.88 | 0.39 | 0.42 |
| 176 | −0.27 | −0.12 | 0.46 | 0.42 |
| 193 | −0.27 | −4.82 | 0.06 | 0.42 |
| 194 | −0.27 | −4.82 | 0.06 | 1.12 |
| 270 | 0.31 | −4.82 | 0.06 | 0.42 |
| 276 | 0.31 | −4.82 | 0.06 | 0.42 |
| 277 | 0.31 | −4.82 | 0.06 | 0.42 |
| 284 | −0.27 | −4.82 | 0.06 | 0.42 |
| 291 | 0.31 | −4.82 | 0.06 | 0.42 |
| 293 | 0.31 | −4.82 | 0.06 | 0.42 |
| 294 | 0.52 | −4.82 | 0.06 | 0.42 |

The table shows the ranges of values of the four parameters $\sigma_p R_1$, $\pi R_2$, $\sigma_m R_2$, and $\pi R_4$ in the KY compounds whose activity for inhibiting HIV infection was tested. The range of values consistent with measured activity for the compounds are: $\sigma_p R_1$, between −0.37 and 0.52; $\pi R_2$, between about 0 and −5; $\sigma_m R_2$, between about −0.1 and 0.6; and $\pi R_4$, between about 2 and −5. Representative having these ranges of $\sigma_p$, $\pi$, and $\sigma_m$ values are given for example in Table VI-I (Hansch, 1979).

The positive coefficient for $\sigma_p$ at $R_1$ predicts greater activity (higher log $(1/ED_{50})$) for polar, oxygen-containing chemical-group substituents, such as esters, acetals, and ketones which have relatively high $\sigma_p$ values. Also of interest at this position are halocarbons, such as —OCF$_3$, with a $\sigma_p$ of 0.35, or —CF$_3$, with a $\sigma_p$ of 0.54. Neither the size nor hydrophobicity of the tested substituents at position $R_1$ were found to have a significant effect on activity, thus allowing for a wide range of possible substituents, provided that the effect on electronic system of the ring, particularly at the position para to $R_1$ is regulated. At the other positions, the electronic effect at $R_2$ was also important. The negative coefficient indicates greater activity for substituents which have negative $\sigma_n$ values.

The hydrophobicity of the $R_2$ and $R_4$ predictors were also relatively important to the bioactivity. The negative coefficient for $\pi$ at $R_4$ predicts greater activity for polar chemical groups with negative partition coefficients.

The analysis also indicates that the $R_1$, $R_2$, $R_3$, and $R_4$ substituents should be selected such that the value of the expression: $1.157\sigma_p R_1 + 0.113\pi R_2 - 2.060\sigma_m R_2 - 0.073\pi R_4 - 0.77 - 1$, is greater than (more positive than about −2.7) and preferably between about −2.7 and −0.9.

The above equation can be used to predict other macrocyclic compounds which should show high activity. One of these compounds is shown in 8A, where $R_1$=OCOCH$_2$(CH$_2$)$_6$CH$_3$ ($\sigma p$=0.31); $R_2$=SO$_3$CH$_3$ ($\pi$=−0.12, $\sigma$m=0.36); $R_3$=H; and $R_4$=CCH$_2$SO$_3$Na ($\pi$=−4.53). This compound has an expected log(-1/ED$_{100}$) value of −0.83, which is in the range of the most active KY compounds tested.

Figure 8A:
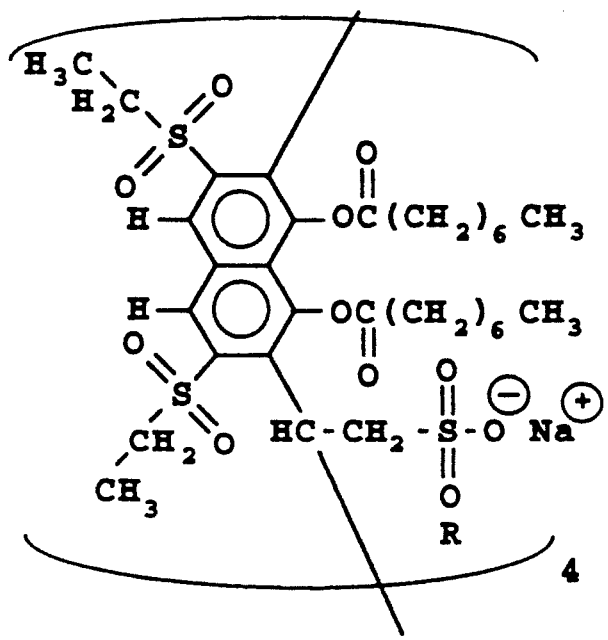
FIGS. 8A and 8B show subunit structures of two macrocyclic compounds predicted by QSAR analysis to have high (8A) and moderate (8B) anti-HIV activity.
Figure 8B:
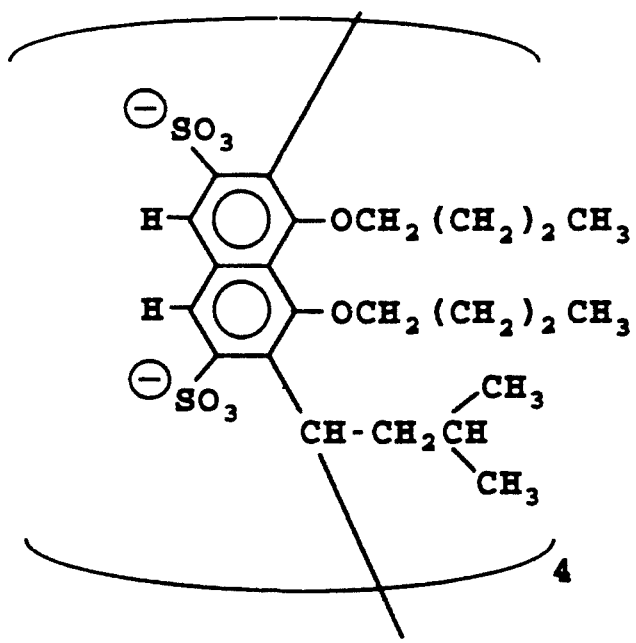

FIG. 8B shows a representative macrocyclic compound which is expected to have moderate anti-HIV activity, in accordance with the invention. The R-group substituents in the compound are $R_1$=OCH$_2$(CH$_2$)$_2$CH$_3$ ($\sigma p$=−0.27); $R_2$=SO$_3$ ($\pi$=−4.82, $\sigma$m=−0.1); $R_3$=H; and $R_4$=CCHCH$_2$CH(CH$_3$)$_2$ ($\pi$=2.76). This compound has an expected log(1/ED$_{100}$) value of −1.60.

IV. Method of Treatment

In another aspect the invention includes a method of inhibiting cell infection by an enveloped virus, by administering to the site of infection a therapeutically effective dose of a macrocyclic chromotropic acid derivative compound. The compound preferably has the form:

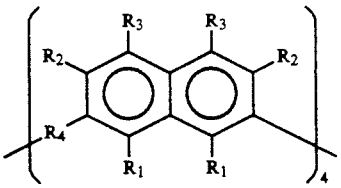

where $R_1$ is OH or an uncharged, carbon-containing substituent containing a oxygen atom linked directly to the naphthalene ring, $R_2$ is sulfonic acid, a sulfonate salt, or a sulfonamide, $R_3$ is H or an uncharged or negatively charged substituent with a log octanol/water partition coefficient value less than 1, and $R_4$ is a 1 to 3 atom bridge linking each naphthalene groups through a naphthalene-ring carbon-methylene linkage.

The method is useful in the treatment of virus infection in a mammalian subject, by virtue of the ability to block infection of host cells by an enveloped virus, and to block the spread of viral infection which occurs by viral lysis of infected cells and release of new virus. The compound used in the method may be administered topically, for example, in the treatment of herpes virus infection. Alternatively, the compound may be administered orally or parenterally, for delivery of the compound to the bloodstream. In another embodiment, the compound is administered intranasally, or by direct application to mucosal tissue, or by inhalation for uptake by the lungs.

The dosage which is administered is a pharmaceutically effective dose, defined as a dose effective to inhibit viral infection of host cells. As seen above, compound doses in the range 1–50 μg/ml are generally effective in inhibiting viral infection of cells. Thus, for many applications, an effective dose would be one which produces a concentration of compound in this range at the site of infection. For topical administration, a composition containing between 1–5% or more KY compound is suitable.

The method of the invention, for treatment of HSV-1 or HSV-2 infection, is detailed in the above-cited patent application for "Treatment for Herpes Simplex Virus." Briefly, it was shown that a KY compound, when administered intravenously, (a) is cleared relatively slowly from the bloodstream, (b) is present predominantly in free form, and (c) retains activity in the bloodstream for inhibiting HSV infection. It was further shown that the drug, 2.5 hours after oral administration, was available in the plasma in active form.

In another treatment method, for inhibiting HSV lesions on an exposed region of a subject, an inhibitory KY compound was contacted with HSV virus by applying the compound to the exposed region of the subject. Animals were infected intravaginally with HSV-2, then treated topically three times daily beginning 6 hours or 48 hours after inoculation with HSV-2. Drug treatment was either saline control, formulated with a suitable vehicle, KY-1, or acyclovir. Swabs of vaginal secretion were obtained and assayed for viral activity by a standard CPE assay. The severity of genital lesions was scored on a 0–5+ scale through a 21 day period of primary infection.

Three to four days after HSV-2 inoculation, vesicular lesions appeared on the external genital skin. Lesions progressed to an ulcerative stage by days 7–8 and gradually healed by days 15–21. The effect of topical treatment with the KY-1 preparations on lesion development and severity is shown in Table 8. The group treated with placebo at +6h had a significantly increased lesion score-day AUC (P <0.05); however, mean peak lesion scores were not different when compared to the untreated control group. Lesion development as determined by both AUC values and mean peak lesion scores was significantly reduced by treatment with 5% KY when given at 6h after infection compared to the placebo (P <0.001). Treatment with 1% KY-1 significantly reduced the AUC at +6h (P <0.01) but not mean peak lesion scores.

TABLE 8

| Treatment | Lesion Score Day Area Under Curve | P-Value | Mean Peak Lesion Score | P-Value |
|---|---|---|---|---|
| Control | 37.0 | — | 3.6 | — |
| Placebo +6 h | 47.0 | <0.05 | 3.9 | NS |
| Placebo +48 h | 42.8 | NS | 3.6 | NS |
| KY 5% +6 hr | 3.8 | <0.001 | 0.8 | <0.001 |
| KY 5% +48 h | 45.7 | NS | 3.7 | NS |
| KY 1% +6 h | 30.8 | <0.01 | 2.9 | NS |
| KY 1% +48 h | 46.6 | NS | 4.3 | NS |
| ACV 5% +6 h | 2.7 | <0.001 | 0.6 | <0.001 |
| ACV 5% +48 h | 45.8 | NS | 3.8 | NS |

No sign of any skin irritation from any of the formulations was observed. Throughout the treatment period, the genital skin remained normal in appearance; no redness or swelling was observed. The guinea pigs also remained normal and healthy in appearance throughout the entire study.

The following examples illustrate methods of preparing tetrameric macrocyclic compounds, in accordance with the invention, and thie use in inhibiting cell infection by enveloped viruses. The examples are intended to illustrate but not limit the scope of the invention.

Materials

All chemical reagents were obtained from Aldrich Chemical Co., or from other commercial sources.

EXAMPLE 1

Preparation of Anti-Viral Compounds

A. KY-1 ($R_1$=OH, $R_2$=$SO_3Na$, $R_3$=H, $R_4$= —$CH_2$—)

To a 41 mM aqueous solution (50 ml) of disodium chromotropic acid, 15 ml of 37% formaldehyde was added, giving a final molar ratio of 5:1 formaldehyde:chromotropic acid. The mixture was reacted with stirring in a stoppered flask at room temperature for 1 week. The resulting dark red solution (70 ml) was filtered under vacuum, and the filtrate, after being concentrated was precipitated by adding 200 ml of acetonitrile. The precipitated product was collected by filtration and taken to dryness under vacuum. The yield of KY-1 was 95%. The compound was characterized as follows:

Melting point (M.P.)>300° C.;
HPLC in $CH_3CN/MeOH/H_2O/TFA$: 14'48" single peak;
(IR/KBr)=3425 (OH), 1638 (Ar), 1181, 1044 ($SO_3$) cm$^{-1}$;
UV ($H_2O$): 238.0, 358.5 nm
Mol Weight: 1505 (M+1) by mass spectroscopy;
$H^1$ NMR($CD_3OD$), chemical shifts on the scale: 5.20 ($CH_2$, 8.01 (ArH) ppm;
$C^{14}$ NMR ($D_2O$), chemical shifts on the $\gamma$ scale: 27.19, 120.18, 121.69, 122-06, 122-67, 133-30, 142.97, and 154.42 ppm.
Analysis ($C_{11}H_6O_8S_2Na_2$)$_4$—$6H_2O$ or ($C_{11}H_6O_8S_2Na_2$)$_8$—$6H_2O$ Found: C 33.17, H 2.54, Na 11.93. Calculated: C 32.75, H 2.23, Na 11.41.

B. KY-3 ($R_1$=OH, $R_2$=$SO_2NH_2$, $R_3$=H, $R_4$= —$CH_2$—)

KY-1 (2 mM) was treated with 5 ml chlorosulfonic acid and the mixture was stirred at room temperature for one-half hour. DMSO (10 ml) was added slowly to the mixture which was subsequently stirred at 80° C. for 1 hour. The resultant mixture was added with 100 ml acetonitrile to precipitate the product which was collected by filtration and then washed with ether.

The crude product was dissolved in 100 ml of 25% ammonium water solution and allowed to react for 2 hours at room temperature. The mixture was concentrated in vacuo and the remaining oil was dissolved in a small amount of water and filtered. The product was precipitated by adding acetonitrile to the filtrate and collected by filtration and washing with acetonitrile. The compound was characterized as follows:

Melting point (M.P.)>300° C.;
Mass spec: 1452 (M-7NH$_2$);.
HPLC in $CH_3CN/MeOH/H_2O/TFA$: 11'46" single peak; (IR/KBr)=3430 (OH), 3187, 1686 (NH$_2$), 1637 (Ar), 1211, 1110, 1044 ($SO_3$) cm$^{-1}$;
UV ($H_2O$): 246 nm;
$H^1$ NMR($D_2O$), chemical shifts on the $\gamma$ scale: 5.15 ($CH_2$), 7.5–8.2 (ArH) ppm;
Analysis: ($C_{44}H_{40}O_{26}S_{10}Na_4$)—$4H_2O$ Found: C 28.62, H 3.93, N 8.82, S 17.17, Na 5.44; Calculated: C 28.51, H 3.89, N 9.07, S 17.28, Na 4.97;

C. KY-42 ($R_1$=OH, $R_2$=$SO_3Na$, $R_3$=H, $R_4$=>CHCOOH)

Chromotropic acid, disodium (10 mM) in 50 ml water was mixed with glyoxylic acid (10.0 mM, in 5 ml water) and 10 ml of 37% hydrogen chloride at room temperature. The mixture was boiled for 8 hours and the color of the solution turned to dark red. The resultant solution was added to 50 ml of water and filtered. The filtrate was concentrated and ethanol was added to precipitate the product of KY-42. The yield was 87%. The compound was characterized as follows:

Melting point (M.P.)>300° C.;
Mass spec: 1623 (M-3H$_2$O).
HPLC in $CH_3CN/MeOH/H_2O/TFA$: 10'36" single peak; (IR/KBr)=3452 (OH), 1801, 1719 (Co), 1638 (Ar), 1206, 1050 ($SO_3$) cm$^{-1}$;
UV ($H_2O$): 238.0, 351.5, 520 nm;
$H^1$ NMR($D_2O$), chemical shifts on the $\gamma$ scale: 7.10 (CHCO$_2$H) 8.00 (ArH) ppm;
$C^{14}$ NMR ($D_2O$), chemical shifts on the $\gamma$ scale: 116.04, 118.90, 120.94, 121.27, 122.30, 124.30, 124.68, 126.60, 128.37, 136.48, 136.71, 140.50, 143.93, 144.26, 145.75, 152.01, 154.33, 156.01, 156.67;
Analysis: ($C_{12}H_6O_{10}S_2Na_2$)$_4$-$4H_2O$ Found: C 32.74, H 2.50; Calculated: C 32.88, H 1.83;

D. KY-123 ($R_1$=OH, $R_2$=$SO_2H$, $R_3$=H, $R_4$= —$CH_2$—)

KY-1 (2 mM) was treated with 5 ml chlorosulfonic acid and the mixture was stirred at room temperature for one-half hour. DMSO (10 ml) was added slowly to the mixture which was subsequently stirred at 80° C. for 1 hour. The resultant mixture was added with 100 ml acetonitrile to precipitate the product which was collected by filtration and then washed with ether. The crude sulfonyl chloride product was treated with sodium sulfite (20 mM) in 4 ml water. The reaction mixture was kept slightly alkaline by addition at intervals of small portions of 50% NaOH for 2 days. After solvent removal, ethanol was added to precipitate the product, which was acidified by addition of 50% $H_2SO_4$, followed by addition of ethanol to precipitate sodium sulfate. The ethanol phase was mixed with ether (1:2, v/v) to precipitate the desired product. Product yield was 39%.

E. KY-147 ($R_1$=OH, $R_2$=$SO_2NHCH_3$, $R_3$=H, $R_4$=—$CH_2$—).

N-methylchromotropic acid chloride was formed by reacting chromotropic acid (disodium salt) with sulphonylchloride in the presence of DMF. The reaction was carried out with stirring at 80° C. for 4 hours. After removal of solvent and excess of thionylchloride in vacuo, acetonitrile was added to precipitate the chromotropic acid chloride which was subsequently collected by filtration and washed with ether. The crude product was added to 20 ml of methylamine and stirred for 2 hours. After removal of all solvent from the resultant substance, the residue was dissolved in a 200 ml of cold methanol and filtered. The filtrate was added with acetonitrile to precipitate the product-N-methylchromotropic acid. Yield 56%.

N-methylchromotropic acid (2 mM) in 3 ml water was reacted with 37% formaldehyde (1 ml) at room temperature for one week. Acetonitrile was added to precipitate the product which was collected by filtration and washed by acetonitrile. Yield was 85%.

F. KY-151 ($R_1$=$OCH_3$, $R_2$=$SO_3Na$, $R_3$=H, $R_4$= —$CH_2$—).

Chromotropic acid, disodium (50 mM) was dissolved in 80 ml of NaOH water solution (0.2M NaOH) and heated to 50° C., dimethylsulfate (0.2M) was added slowly for 1 hour. The mixture was continuously stirred for another 2 hours and left at room temperature for 2 days. Saturated NaCl solution (100 ml) was added to the resultant substance and filtered. The precipitate was washed with ethanol, acetonitrile and ether sequentially. The dry substance was dissolved in 100 ml of methanol and filtered. The filtrate was concentrated and ether was added to precipitate the dimethyl ether of chromotropic acid, disodium. The yield of the dimethylether of chromotropic acid was 71%.

Dimethylether of chromotropic acid, disodium (2.3 mM) dissolved in 5 ml DMF was treated with treated with 1 g para-formaldehyde in the presence of acetic acid (15 ml) at 80° C. for 12 hours. The product was precipitated and isolated as in Example 1A. The product yield was 32%.

G. KY-143 ($R_1$=OH, $R_2$=$SO_2Na$, $R_3$=H, $R_4$= —$CH_2$—).

Chromotropic acid (3 mM) in 5 ml DMF was treated with 3 ml of thionylchloride at 80° C. for 4 hours. After removal of solvent and excess thionylchloride in vacuo, acetonitrile was added to precipitate the chromotropic acid chloride which subsequently collected by filtration and washed with ether. The crude product was added to a solution containing 6 g anhydrous sodium sulfate, 4.2 g sodium bicarbonate in 24 ml $H_2O$ at 70°-80° C. When addition was complete, the mixture was heated and stirred at 80° C. for 1 hour, then stored overnight at room temperature. After removal of all the solvent, 200 ml methanol was added to precipitate the crude product, which was then treated with HCl solution at room temperature. Acetonitrile was added to precipitate the crude product. The latter was treated with 37% formaldehyde at room temperature under nitrogen for 1 week. Product yield was 38%.

H. KY-158 ($R_1$=OH, $R_2$=$SO_2CH_3$, $R_3$=H, $R_4$= —$CH_2$—).

KY-1 from Example 1A was first treated with thionyl chloride to produce chromotropic acid sulfonyl chloride. This compound was reduced by excess sodium sulfite in the presence of sodium bicarbonate to produce the corresponding sodium sulfonate salt of chromotropic acid ($R_2$=$SO_2Na$). The sulfonate salt was treated with sulfonyl chloride to produce the sulfonyl chloride. The product was dissolved in methanol and treated with sodium methoxide in methanol under nitrogen. The product was worked up as described in Example 1A. Product yield was about 21%.

I. KY-175 ($R_1$=OH, $R_2$=$SO_3CH_3$, $R_3$=H, $R_4$= —$CH_2$—).

KY-1 from example 1A was first treated with thionyl chloride to produce chromotropic acid sulfonyl chloride. This compound was then treated with sodium methoxide in methanol in the presence of sodium salt. The product was worked up as described in Example 1A. Product yield was about 29%.

J. KY-270 ($R_1$=$OCOCH_3$, $R_2$=$SO_3Na$, $R_3$=H, $R_4$= —$CH_2$—).

KY-1 from Example 1A (0.66 mmole) was dissolved in 3 ml water containing 0.1 g NaOH. To this was added 1 g acetic chloride (13 mmole) and the reaction was allowed to proceed at room temperature overnight with stirring. After solvent removal, 25 ml ethanol was added to precipitate the product. The crude product was dissolved in methanol and filtered. The filtrate was allowed to precipitate, giving a 87% yield.

K. KY-346 ($R_1$=OH, $R_2$=$SO_3Na$, $R_3$=H, $R_4$= —$CH_2$—N($CH_3$)—$CH_2$—)

Chromotropic acid disodium salt, was dissolved in 80 ml of water at a concentration of 50 mM with stirring at 50° C. until the solution turned to clear, hexamethylenetetramine (50 mM) was then added to above solution with continuous stirring at the same temperature for additional two hours. At this time, the color of this mixture converted to dark blue. The mixture was allowed to stir at room temperature for 2 days. The resultant dark blue solution was filtered and the filtrate was concentrated, evaporated by flask, which was subsequently treated with 200 ml methanol to precipitate the product KY-346. The yield of KY-346 was 85%. The compound was characterized as follows:

M.P.>300° C.;

HPLC in $CH_3CN$/MeOH/$H_2O$/TFA: 13'07" single peak;

(IR/KBr)=3425 (OH), 1626 (Ar), 1197, 1052 ($SO_3$) $cm^{-1}$;

UV ($H_2O$): 232.0, 377.5 nm

Analysis: ($C_{13}H_{11}O_8S_2Na_2$)$_4$·6$H_2O$ Found: C 33.17, H 2.13, N 2.75, Na 11.51 Calculated: C 37.23, H 2.63, N 3.34, Na 10.98.

Molecular weight: 1656 by gel filtration.

EXAMPLE 2

Cytotoxicity in Proliferating Cells

A panel of human cell lines was used to check the toxicity of the drugs, including: KB (nasopharyngeal carcinoma), HeLaS$_3$ (cervical epithelial carcinoma), PLC (hepatocarcinoma), HepG$_2$ (human hepatocarcinoma) HepG$_2$T$_{14}$ (hepatocarcinoma transfected with HBV), WI38 (normal human lung fibroblast), BT549 (breast cancer), SW480 (breast cancer), and A549 (lung cancer).

$5 \times 10^4$ cells were plated in each well of a 24 well multi-dish in 1 ml of RPMI-1640 containing 5% FCS and P/S. On the second day after plating, one of the thirty test compounds given in Table 1 below was added to the cells, at concentrations between 1–100 µg/ml. Three days later, the medium was removed and the cells were stained with Commassie Blue in 40% methanol and 10% acetic acid. The results are discussed in Section II above.

EXAMPLE 3

Inhibition of HSV Activity: Cytopathic Effect

Vero cells were maintained in RPMI-1640 medium supplemented with 5% fetal calf serum, 100 Units of penicillin per ml and 100 µg of streptomycin per ml at 37° C. in a humidified incubator containing 7% CO$_2$. The HSV strains HSV-1 (Kos-1) and HSV-2 (333) were used.

$1 \times 10^5$ Vero cells were plated in each well of a 96 well microtitre plate in 0.2 ml RPMI-1640 medium containing 5% FCS and 0.1% methyl cellulose (15 cps). After overnight incubation, and cell doubling, the medium was aspirated and replaced with 100 µl of the same medium containing 2% FCS, and 50 µl control or drug solution to a final drug concentration of 10 µg/ml and 50 µl virus, containing about 3 PFU/cell, i.e., $6 \times 10^5$ PFU/well, of HSV-1 or HSV-2.

The cells were cultured for 24 hours at 37° C., at which time cytopathic effects are clearly visible. In the absence of viral infection, the cells form an even monolayer of fibroblast cells. With viral infection, the cells form a suspension of round cells, followed by cell clumping, whose appearance is easily distinguishable from normal fibroblast cells. If no detectable cytopathic effect was produced, the test was repeated with 20 µg/ml. A parallel set of cells without virus inoculation were done as a control for cytotoxicity to Vero cells.

Table 1 above shows the structures of the compounds which were tested, and Table 2, column 2, the compounds which protected the cells from cytopathic effect (+).

EXAMPLE 4

Inhibition of HSV Activity: Plaque Reduction

Vero cells were maintained in RPMI-1640 medium supplemented with 5% fetal calf serum, as in Example 3. $4 \times 10^5$ Vero cells were plated in a 24-well plate, in 1 ml RPMI-1640 medium containing 5% FCS and 0.1% methyl cellulose (15 cps). After overnight incubation, and cell doubling, the medium was aspirated and replaced with 100 µl of the same medium containing 2% FCS, which contained 50 µl control or drug solution to a final drug concentration of 10 µg/ml and 50 µl virus, containing about 3 PFU/cell, i.e., $2.4 \times 10^6$ PFU/well, of HSV-1 or HSV-2, as in Example 3.

After 2 hrs. at 37° absorption the virus and the drugs were removed and the cells were washed with PBS and 0.5 ml of 1% methylcellulose (4K cps) in RPMI-1640+2% FCS+penicillin/streptomycin (P/S) was added. Two days later, the media were removed. The cells were stained with 0.8% crystal violet in 50% ethanol. The plaques formed were counted and the percentage of inhibition was calculated by dividing by the plaques formed in control. ED$_{50}$ values, indicating the concentration of drug needed to produce 50% inhibition of viral plaques, were calculated assuming a linear dose response for viral plaque inhibition. The calculated ED$_{50}$ values are given in Table 2 above.

EXAMPLE 5

Inhibition of HSV Activity: Viral Yield Inhibition $1 \times 10^6$ HeLa S$_3$ were plated in 25 T flasks in 5 ml RPMI-1640+5% FCS+P/S. 24 hours later, the medium was aspirated and replaced with $6 \times 10^6$ PFU HSV-1 or HSV-2, and serial dilutions of selected KY compounds, at 10, 5, 2.5, 1.25, and 0.625 µg/ml drug. After growth at 37° C. for 24 hours in 2 ml of RPMI-1640 containing 2% FCS and P/S, the cells were frozen at −70° C. until the time for titration. The cells were freeze/thawed 3 times to release virus from the cells, and serially diluted 10 fold.

$1 \times 10^5$ Vero cells were plated in each well of 24 well multi-dish in 1 ml RPMI-1640+5% FCS+P/S+0.1% methylcellulose (15 cps). On the second day, after removal of the medium, the 10 fold serially diluted virus in 100 µl was added in duplicate. After 2 hours incubation at 37° C., the virus was removed and 0.5 ml methycellulose (4K cps) in RPMI-1640 and 2% FCS+P/S was added. Two days later, the medium was removed. The cells were stained in 0.8% crystal violet in 50% ethanol. The plaques formed were counted and the titer was calculated from the fold of dilutions.

The reduction in virus yield, as a function of KY compound concentration, is seen in FIGS. 3A–3E for five of the KY compounds tested.

EXAMPLE 6

Activity Against Drug-Resistant Strains of HSV-1 and HSV-2

The following strains of HSV-1 and HSV-2 virus were used: KOS, a wild type HSV-1 virus; KOS (PMEA) and KOS (PFA), both drug-resistant HSV-1 viruses having a DNA polymerase mutation; 333, a wild type HSV-2 HSV-2 virus, and 333 (DHPG), a drug-resistant HSV-2 virus having a thymidine kinase mutation.

Inhibition of viral yield was by KY-1, acyclovir (ACV), DHPG, PFA, and PMEA was examined in each of the five HSV strains substantially as described in Example 5. Briefly, Hela S$_3$ were plated in 25 T flasks in culture, and 24 hours later, the medium was aspirated and replaced with $6 \times 10^6$ PFU of the selected HSV strain, and serial dilutions of KY-1, ACV, DHGP, PFA, and PMEA. After growth at 37° C. for 24 hours in 2 ml of RPMI-1640 containing 2% FCS and P/S, the cells were frozen at −70° C. until the time for titration. The cells were freeze/thawed 3 times to release virus from the cells, serially diluted 10 fold, and the serial dilutions were added to Vero cells in culture. After 2 hours incubation at 37° C. the virus was removed and 0.5 ml methycellulose (4K cps) in RPMI-1640 and 2% FCS+P/S was added. Two days later, the medium was removed. The cells were stained in 0.8% crystal violet in 50% ethanol. The plaques formed were counted and the titer was calculated from the fold of dilutions. From the drug dose response, the concentration of each drug required to effect a 90% inhibition of virus yield, the $IC_{90}$ concentration was determined. These values are shown in Table 3 above.

EXAMPLE 7

Inhibition of RSV Activity

Assays to assess the antiviral activity of LY253963 in tissue culture were perormed in 96-well flat-bottom tissue culture plates (Falcon 307), using conditions similar to those used in the cytotoxicity assays described above. In these assays, LY253963 was tested in quadruplicate by serially diluting the compound in 2% FCS-MEM using serial two-fold dilutions (0.05 ml/well). A 0.05 ml volume of the appropriate virus containing approximately 100 median tissue culture inectious doses ($TCID_{50}$) was then added to all wells but thos4e set aside as antiviral and tissue control wells. Next, approximately $3 \times 10^3$ HEp2 cells (0.1 ml) were added to each well. Control wells containing antiviral and no virus (antiviral control), containing virus but no antiviral (virus control), or containing medium without virus or antiviral (tissue control), were included in each test. The challenge virus was then back titrated. All assay plates were incubated at 35° C. for 5 to 7 days in a 5% $CO_2$ incubator. When virus control wells exhibited 70% to 100% CPE including syncytia, all wells were observed. The median efficacious dose ($ED_{50}$) was calculated after determining the final concentration of antiviral in the last wells in each set of quadruplicate rows exhibiting <50% CPE compared to the CPE in virus control wells. The $ED_{50}$ values calculated for each of the compounds tested are shown in Table 5.

EXAMPLE 8

Inhibition of Influenza A Activity

The anti-influenza A activity of KY compounds was evaluated as described in Example 7, except that MDCK cells (kidney cell line) ws used for infection in vitro by influenza virus (strain A/Taiwan).

EXAMPLE 9

Inhibition of HIV-Induced Cell Fusion

Human $CD_4^+$ indicator cells (VB) and chronically infected $H_9$ cells were maintained in RPMI-1640 medium supplemented with 5% fetal calf serum, 100 Units of penicillin per ml and 100 µg of streptomycin per ml at 37° C. in a humidified incubator containing 7% $CO_2$. The HIV strains that were used were HTLV-III$_B$ and RF-II strains obtained from the National Institutes of Health (Bethesda, Md.).

For the fusion assay, serial dilutions between 1:2 and $1:2^8$ of a selected KY compound, 1 mg/ml in PBS were made in a 96 well round bottom plate. The diluted KY compound was transferred to a 96 well flat-bottom plate. To each well was added 25 µg chronically infected $H_9$ cells (at $2 \times 10U6$, cells/ml), or cells chronically infected with RF-II strain HIV, followed by incubation at 37° C. for 45 minutes. To each well was then added 25 µl VB cells (about $5 \times 10^4$ cells), and the cells and virus isolates were cocultured for 18 hours in a humid 5% $CO_2$ atmosphere. The extent of syncytia formation was scored under phase microscopy, and the concentration which completely inhibited syncytia formation ($ED_{100}$) was recorded. The results are given in Table 6.

Although the invention has been described with reference to preferred compounds and method of virus inhibition employing the compounds, it will be appreciated that various modification and changes may be made without departing from the invention.

We claim:

1. A method of inhibiting cell infection by an enveloped virus comprising
    administering to the site of infection a therapeutically effective dose of a macrocyclic chromotropic acid derivative.

2. The method of claim 1, wherein the chromotropic acid derivative has the form:

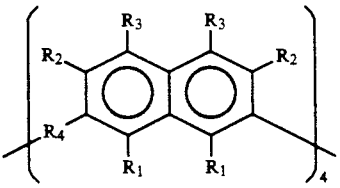

where
    $R_1$ is OH or an uncharged, carbon-containing substituent containing a oxygen atom linked directly to the naphthalene ring,
    $R_2$ is sulfonic acid, a sulfonate salt, or a sulfonamide,
    $R_3$ is H or an uncharged or negatively charged substituent with a log octanol/water partition coefficient value less than 1, and
    $R_4$ is a 1 to 3 atom bridge linking each naphthalene groups through a naphthalene-ring carbon-methylene linkage.

3. The method of claim 1, wherein the enveloped virus is selected from the virus families Orthomyxovirus, Paramyxovirus, Retrovirus and Herpesvirus.

4. The method of claim 1, wherein the enveloped virus is selected from the group consisting of HSV-1, HSV-2, Human Immunodeficiency virus (HIV), Influenza A, Influenza B, and Respiratory Syncytial Virus (RSV).

* * * * *